United States Patent [19]

Kawamura et al.

[11] Patent Number: 5,269,312
[45] Date of Patent: Dec. 14, 1993

[54] PRESSURE PULSE WAVE TRANSMITTING SHEET USED WITH PRESSURE PULSE WAVE SENSOR

[75] Inventors: Norio Kawamura, Nagoya; Hideto Tsuchida, Gifu; Tsuneo Nakagawa, Kani; Ye Aung, Komaki, all of Japan

[73] Assignee: Colin Electronics Co., Ltd., Japan

[21] Appl. No.: 917,427

[22] Filed: Jul. 23, 1992

[30] Foreign Application Priority Data

Jul. 29, 1991 [JP] Japan .................. 3-67212[U]

[51] Int. Cl.⁵ .................................................. A61B 5/02
[52] U.S. Cl. .................................................. 128/690
[58] Field of Search .................... 128/687–690, 128/748

[56] References Cited

U.S. PATENT DOCUMENTS

| | | | |
|---|---|---|---|
| 2,831,478 | 4/1958 | Uddenberg et al. | 128/748 |
| 3,811,429 | 5/1974 | Fletcher et al. | 128/687 |
| 3,957,713 | 5/1976 | Jeram et al. | |
| 4,481,001 | 11/1984 | Graham et al. | 434/267 |
| 4,536,165 | 8/1985 | Maar . | |
| 4,561,447 | 12/1985 | Kawamura et al. | 128/687 |
| 4,621,029 | 11/1986 | Kawaguchi | 428/447 |
| 4,928,700 | 5/1990 | Harada | 128/672 |
| 5,119,822 | 6/1992 | Niwa | 128/690 |

FOREIGN PATENT DOCUMENTS

| | | |
|---|---|---|
| 0120137 | 10/1984 | European Pat. Off. . |
| 3-27208 | 3/1991 | Japan . |
| 729556 | 5/1955 | United Kingdom . |
| 1147072 | 4/1969 | United Kingdom . |
| 1571643 | 7/1980 | United Kingdom . |
| 2118068 | 10/1983 | United Kingdom . |

Primary Examiner—Lee S. Cohen
Assistant Examiner—Marianne Parker
Attorney, Agent, or Firm—Oliff & Berridge

[57] ABSTRACT

A pressure pulse wave transmitting sheet for being interposed between a skin surface of a living subject such as a patient and a pressure pulse wave sensor set on the skin surface in pressed contact therewith, the sensor having a press surface in which at least one pressure sensing element is provided and which is pressed against the skin surface so that the at least one pressure sensing element detects a pressure pulse wave transmitted from an artery of the subject underlying the skin surface, to the press surface via the sheet, the sheet being formed of an elastic material having a hardness substantially equal to a hardness of human being's skin.

15 Claims, 3 Drawing Sheets

PRESSURE PULSE WAVE TRANSMITTING SHEET USED WITH PRESSURE PULSE WAVE SENSOR

BACKGROUND OF THE INVENTION

1. Field of the Invention

The present invention relates in general to the art of detecting a pressure pulse wave of a living subject by pressing a pressure pulse wave sensor against a skin surface of the subject and in particular to a pressure pulse wave transmitting sheet for being interposed between the sensor and the skin surface.

2. Related Art Statement

There is known a pulse wave detecting device including (a) a pressure pulse wave sensor having a press surface and adapted to be set on a skin surface of a body portion (e.g., wrist) of a patient so as to be positioned directly above an arterial vessel (e.g., radial artery) of the patient, and (b) pressing means for pressing the sensor against the artery via the skin so that at least one pressure sensing element provided in the press surface of the sensor detects a pressure pulse wave transmitted from the artery to the press surface in synchronism with heartbeat of the patient and generates an electrical signal representative of the detected pressure pulse wave (hereinafter, referred to as the "pulse wave signal"). An example of this device is disclosed in Japanese Utility Model Application filed by the Assignee of the present application and laid open under Publication No. 3-27208 on Mar. 19, 1991.

However, in the above detecting device, the pressure pulse wave sensor is directly pressed against, or held in direct contact with, the skin of the patient, and accordingly the patient may suffer from pain due to the direct pressing or contact of the sensor with the skin. In addition, in the case where the detecting device is applied to a thin patient, the sensor may not engage deeply with, or bite deeply into, the skin of the patient and consequently the sensor may move or slip off the position directly above the artery.

Furthermore, in the case where the skin on which the sensor is set is covered with hair stiffer than the skin, the pulse wave signal generated from the sensor may adversely be influenced by the hair. More specifically, the magnitude of the pulse wave signal may inaccurately be increased due to the pressed contact of the hair with each pressure sensing element supported by the press surface of the sensor.

SUMMARY OF THE INVENTION

It is therefore an object of the present invention to provide the art of detecting a pressure pulse wave of a living subject with at least one pressure sensing element provided in a press surface of a pressure pulse wave sensor pressed against a skin surface of the subject, wherein the pain or discomfort of the subject due to the pressing of the sensor is effectively reduced, the sensor is prevented from being moved out of position on even a thin subject, and the pulse wave signal is protected against adversely being influenced by a hairy skin of a subject, and in particular to provide a pressure pulse wave transmitting sheet for being interposed between the sensor and the skin surface.

According to a first aspect of the present invention, there is provided a pressure pulse wave transmitting sheet for being interposed between a skin surface of a living subject and a pressure pulse wave sensor set on the skin surface in pressed contact therewith, the sensor having a press surface in which at least one pressure sensing element is provided and which is pressed against the skin surface so that the at least one pressure sensing element detects a pressure pulse wave transmitted from an artery of the subject underlying the skin surface, to the press surface via the sheet, the sheet being formed of an elastic material having a hardness substantially equal to a hardness of human being's skin.

The pressure pulse wave transmitting sheet in accordance with the present invention is used by being interposed between a skin surface of a subject such as a patient and a press surface of a pressure pulse wave sensor pressed against the skin surface. Since the sheet is formed of an elastic material having a hardness substantially equal to a hardness of human being's skin, the sheet effectively reduces the pain or discomfort of the patient due to the pressing of the sensor against the skin, without adversely influencing the detection of pressure pulse wave with the sensor. In addition, the sheet serves like an artificial skin with a suitable thickness, on the true skin of the patient, so that the sensor is allowed to bite into the artificial skin (sheet) on the true skin of even a thin person. Consequently, the sensor is prevented from being moved out of position on the skin. Furthermore, even in the case where the sensor is pressed against a hairy skin of a subject, the hair does not directly contact the press surface (or at least one pressure sensing element) of the sensor, since the sheet is interposed between the sensor and the skin. Thus, the present sheet advantageously prevents a hairy skin from adversely influencing the magnitude of a pulse wave signal generated by the sensor.

According to a second aspect of the present invention, there is provided a method of detecting a pressure pulse wave of a living subject, comprising the steps of (a) interposing a pressure pulse wave transmitting sheet between a skin surface of the subject and a pressure pulse wave sensor set on the skin surface, the sensor having a press surface in which at least one pressure sensing element is provided, the sheet being formed of an elastic material having a hardness substantially equal to a hardness of human being's skin, and (b) pressing the sensor against the skin surface so that the at least one pressure sensing element detects a pressure pulse wave transmitted from an artery of the subject underlying the skin surface, to the press surface of the sensor via the sheet.

This method provides the same advantages as those with the pressure pulse wave transmitting sheet in accordance with the first aspect of the invention.

According to a third aspect of the present invention, there is provided an apparatus for detecting a pressure pulse wave of a living subject, comprising (A) a pressure pulse wave sensor adapted to be set on a skin surface of a subject in pressed contact therewith, the sensor having a press surface in which at least one pressure sensing element is provided, (B) a pressure pulse wave transmitting sheet interposed between the skin surface of the subject and the press surface of the pressure pulse wave sensor, the sheet being formed of an elastic material having a hardness substantially equal to a hardness of human being's skin, and (C) pressing means for pressing the sensor against the skin surface so that the at least one pressure sensing element detects a pressure pulse wave transmitted from an artery of the subject underlying the skin surface, to the press surface of the sensor via the sheet.

This apparatus provides the same advantages as those with the pressure pulse wave transmitting sheet in accordance with the first aspect of the invention.

In a preferred embodiment of the present invention, the apparatus further comprises a housing supporting the sensor and the pressing means, the housing having an external surface marked with at least two indicias, the sheet having a surface area greater than the external surface of the housing and being marked with a plurality of first parallel straight lines and a plurality of second parallel straight lines which are perpendicular to the first straight lines, each of the first straight lines being associated with a corresponding one of a first series of different indicias, each of the second straight lines being associated with a corresponding one of a second series of different indicias, the housing being set on the skin surface via the sheet such that one of the at least two indicias is aligned with one of the first straight lines and another of the at least two indicias is aligned with one of the second straight lines.

In the above embodiment of the present invention, the sheet may have a quadrangular configuration, and be marked with the first series of different indicias along one of a pair of opposite sides thereof perpendicular to the first straight lines and marked with the second series of different indicias along one of the other pair of opposite sides thereof perpendicular to the second straight lines.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
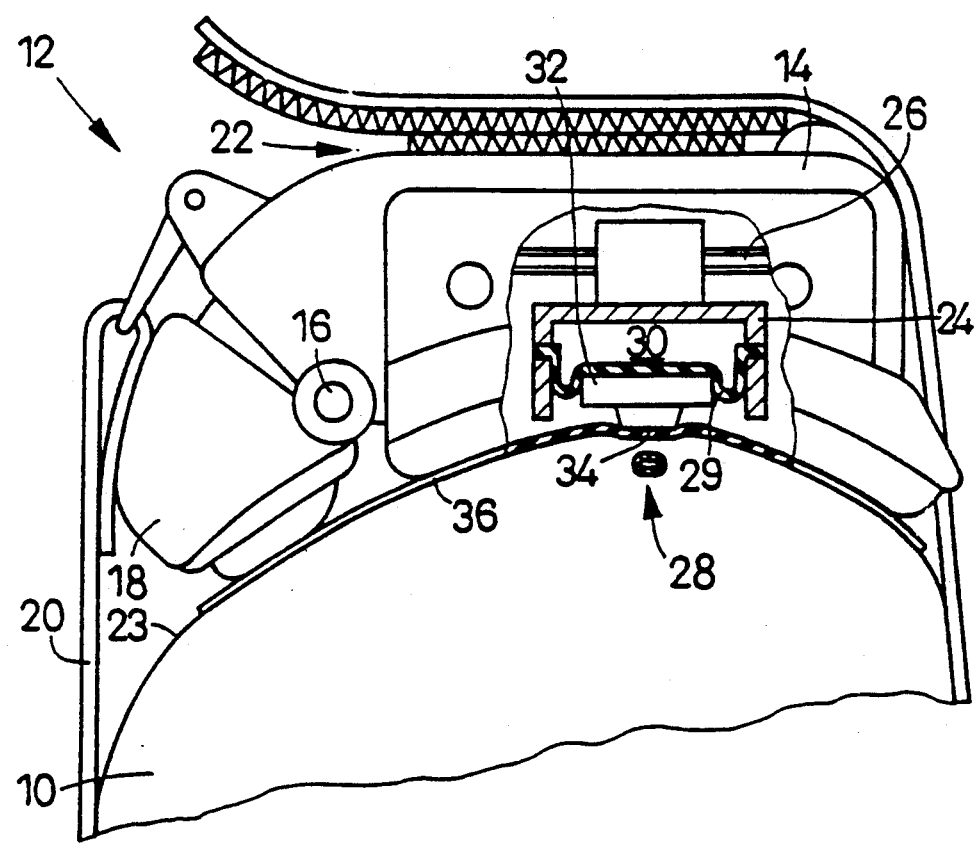
FIG. 1 is a partially recessed, side view of a pulse wave detecting apparatus to which the present invention is applied, which apparatus includes a pressure pulse wave sensor and a pressure pulse wave transmitting sheet.

Referring first to FIG. 1, there is shown a pulse wave detecting apparatus for detecting a pressure pulse wave from a living subject such as a patient. The apparatus includes a pressure pulse wave transmitting sheet 36, and a pressure pulse wave sensor probe 12 adapted to be worn on the patient via the sheet 36.

The sensor probe 12 includes a first and a second housing 14, 18 which are pivotally connected to each other by a pin 16. The first housing 14 as a whole has a container-like configuration. The first housing 14 has an open end adapted to contact a skin surface 23 of a wrist 10 of the patient. A wrist band 20 is connected at one end thereof to the first housing 14. By placing the sensor probe 12 on the wrist 10, winding the wrist band 20 around the wrist 10, and fastening a pair of fastener members 22, 22 respectively provided on the other end of the wrist band 20 and on the outer surface of the bottom wall of the first housing 14, the sensor probe 12 is detachably worn on the skin surface 23 of the patient.

A container-like casing 24 is accommodated in the first housing 14. The casing 24 has an open end which is opposed to the skin surface 23 when the sensor probe 12 is placed on the skin surface 23. The casing 24 is engaged with a feed screw 26 extending along the longitudinal side of the first housing 14, i.e., in a direction generally perpendicular to the direction of extension of a radial artery 28. The casing 24 is also engaged with the side wall of the first housing 14 via guide means such as side rails and guide grooves (not shown). Thus, when the feed screw 26 is rotated by being driven by an electric motor (not shown) accommodated in the second housing 18, the casing 24 is movable in the direction generally perpendicular to the radial artery 28. The first housing 14 also accommodates a reduction gear unit (not shown) which is on one hand operatively connected to one of opposite axial ends of the feed screw 26 located on the side of the second housing 18 and which is on the other hand operatively connected to an output shaft of the above-indicated electric motor via a flexible coupling (not shown). This arrangement ensures that the driving force of the electric motor is transmitted to the feed screw 26 via the reduction gear unit, independent of the relative angular position between the first and second housings 14, 18.

Figure 4:
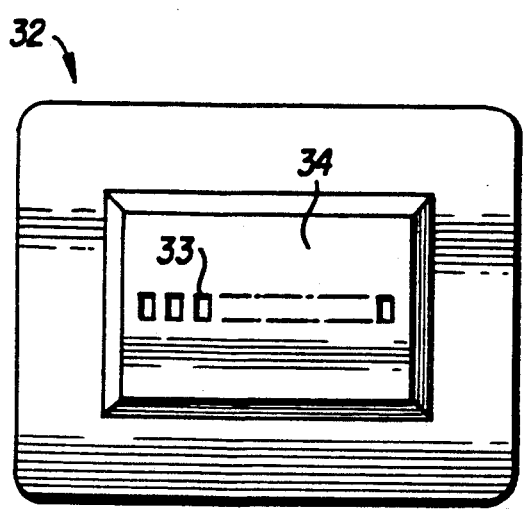
FIG. 4 is a view of the pressure pulse wave sensor of FIG. 1.

An elastic diaphragm 29 is supported by the side wall of the casing 24, so that the diaphragm 29 and the casing 24 cooperate with each other to define a pressure chamber 30 on the side of the bottom wall of the casing 24. To an external surface of the diaphragm 29 away from the pressure chamber 30, a pressure pulse wave sensor 32 is secured. The sensor 32 has, in a press surface 34 thereof, an array of pressure sensing elements 33 (FIG. 4), such as pressure sensing diodes, arranged in the direction of movement of the casing 24. When pressurized fluid such as pressurized air is supplied from a pressurized fluid supplying source (not shown) to the pressure chamber 30 and accordingly the diaphragm 29 is inflated, the sensor 32 is advanceable out of the casing 24 (and the first housing 14), so that the sensor 32 is pressed against the skin surface 23 with a pressing force corresponding to the air pressure in the pressure chamber 30. Specifically, the sensor 32 is pressed against the radial artery 28 via the skin surface 23, so as to partially flatten the wall of the radial artery 28. Each of the pressure sensing diodes 33 detects a pressure pulse wave that is an oscillatory pressure wave transmitted from inside the radial artery 28 to the press surface 34 via the flattened wall of the artery 28 and the skin surface 23, in synchronism with heartbeat of the patient, and produces an electric signal indicative of the detected pressure pulse wave (hereinafter, referred to as the "pulse wave signal").

In the pulse wave detecting apparatus including the pressure pulse wave sensor probe 12 constructed as described above, a control device (not shown) operates for slowly increasing the pressure in the pressure chamber 30 and actuating, based on the pulse wave signals supplied from the individual pressure sensing diodes during the pressure increasing operation, the above-mentioned electric motor so as to move the casing 24 (or the sensor 32) to an optimum position at which a middle portion of the array of pressure sensing diodes 33 is positioned directly above the radial artery 28. In addition, based on the pulse wave signals supplied from the pressure sensing diodes 33 when the pressure in the pressure chamber 30 is slowly increased, the control device determines an optimum pressure to be applied to the pressure chamber 30 of the casing 24, that is, optimum pressing force to be applied to the sensor 32 so as to partially flatten the wall of the radial artery 28. These techniques are known in the art. With the sensor 32 being held at the optimum position and being pressed with the optimum pressing force, a middle one of a middle portion of the array of pressure sensing diodes which portion is located directly above the radial artery 28, is selected as an "ACTIVE" pressure sensing element, and the pulse wave signal from the ACTIVE element is obtained as a pressure pulse wave of the patient. This signal is free of the tensile or elastic force produced in the wall of the artery 28 when the artery 28 is deformed by pulsating blood flow and therefore the signal accurately represents blood pressure inside the artery 28. The technique of selecting the ACTIVE element is also known in the art.

The present apparatus further includes a pressure pulse wave transmitting sheet 36 for being interposed between the sensor probe 12 and the skin surface 23 of the patient. The sheet 36 is formed of an elastic material such as silicone rubber. The sheet 36 has a surface area larger than the area of an external surface of the probe 12 as viewed from a person opposing the outer surface of the bottom wall of the first housing 14, that is, surface area permitting the probe 12 to entirely be placed on the sheet 36. Thus, the sensor 32 is pressed against the skin surface 23 via the sheet 36. The sheet 36 has a thickness of about 0.6 mm to about 3.0 mm, more preferably from about 0.6 mm to about 1.0 mm. In addition, the sheet 36 has a hardness of about 1 degree to about 15 degrees, more preferably from about 5 degrees to about 15 degrees, measured by a JIS (Japanese Industrial Standard) A-type spring-using hardness measuring device according to JIS K 6301 (1975, Physical Testing Methods for Vulcanized Rubber), Section No. 1.2.(3) "Hardness Test". This hardness is comparable to a hardness of human being's skin. Thus, the elastic sheet 36 effectively reduces the pain or discomfort of the patient due to the pressed contact of the sensor 32 with the skin surface 23, without adversely influencing the detection of pressure pulse wave by the sensor 32. Since the silicone rubber sheet 36 produces a large friction force with the skin surface 23, the sheet 36 does not move or slip on the skin surface 32 while the pressure pulse wave is detected via the sheet 36. Therefore, the sheet 36 is not required to be adhered to the skin surface 23 positively, for example, with an adhesive.

As is apparent from the foregoing description, in the present embodiment, the elastic sheet 36 having a hardness substantially equal to that of the patient is interposed between the probe 12 and the skin surface 23. This arrangement contributes to reducing the pain or discomfort of the patient, as compared with an arrangement in which the sensor 32 is directly pressed against the skin surface 23 without interposing the sheet 36 therebetween. In addition, the elastic sheet 36 effectively prevents the probe 12 or the sensor 32 from moving or slipping out of position. Since the sheet 36 serves like an artificial skin with a suitable thickness on the true skin 23 of the patient, the sensor 32 bites deeply into the artificial skin (sheet 36) on the true skin 23. Therefore, the elastic sheet 36 prevents the sensor 32 from moving out of position on even a thin person.

Furthermore, in the illustrated embodiment, the elastic sheet 36 is placed over a hairy skin 23 of a patient, and the sensor 32 is pressed against the hairy skin 23 via the sheet 36. Therefore, the hair of the skin 23 does not directly contact the pressure sensing diodes provided in the press surface 34 of the sensor 32. Thus, the sheet 36 effectively prevents the hairy skin 23 from adversely influencing the pulse wave signals generated from the pressure sensing diodes. If bristly hair directly contacts the press surface 34 (or pressure sensing diodes 33) of the sensor 32, the magnitudes of the pulse wave signals from the pressure sensing diodes 33 are increased inaccurately. In this event, the positioning of the sensor 32 relative to the radial artery 28 and the determination of the optimum pressing force applied to the sensor 32 are carried out inaccurately, and therefore the accuracy of detection of the pressure pulse wave is lowered.

In the case where the sensor probe 12 is used on a number of patients in a hospital by being directly pressed against the skin of each patient, it is possible that a disease is infected from one patient to another via the sensor probe 12. However, in the illustrated embodiment, the probe 12 is set on each patient via the sheet 36. Infection of a disease via the probe 12 can effectively prevented by discarding each sheet 36 used on each patient.

There will be described another embodiment of the present invention.

Figure 2:
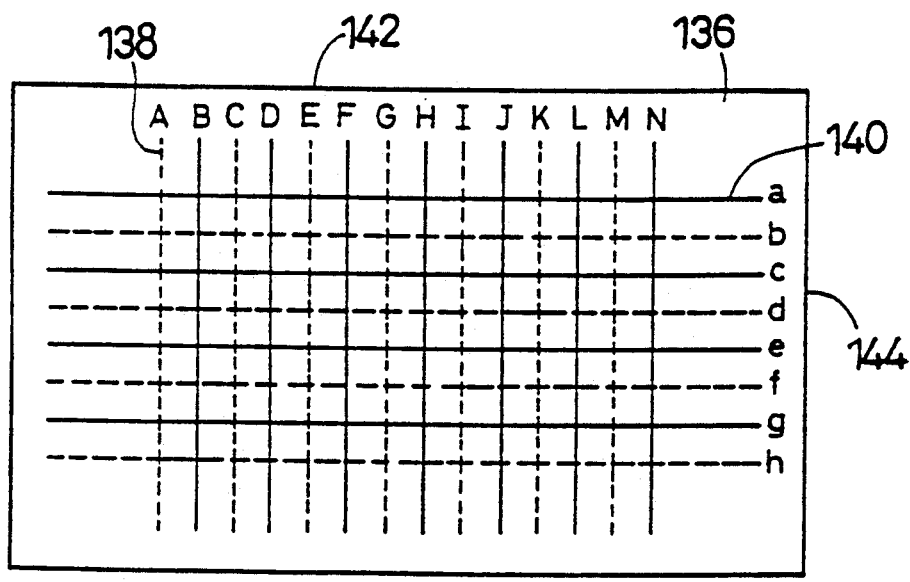
FIG. 2 is a plan view of another pulse wave transmitting sheet.
Figure 3:
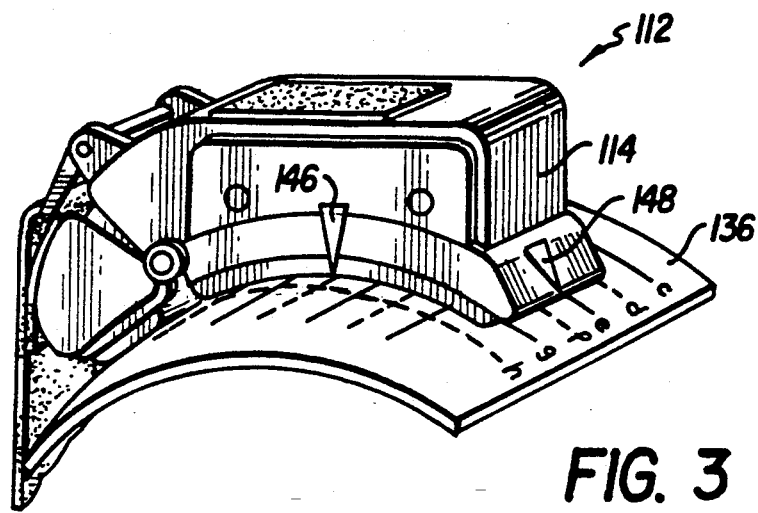
FIG. 3 is a perspective view of another embodiment of the present invention, in which the sheet of FIG. 2 is employed.

FIG. 2 shows another pressure pulse wave transmitting sheet 136 formed of a silicone rubber and having a rectangular configuration. On one of opposite surfaces of the elastic sheet 136, a number of width-wise parallel straight lines 138 and a number of length-wise parallel straight lines 140 are drawn like a lattice such that the width-wise lines 138 are perpendicular to the length-wise lines 140. The sheet 136 is marked with alphabetic capital letters, A to N, along one 142 of the length-wise sides of the quadrangular sheet 136, so as to indicate the corresponding width-wise lines 138, and is marked with alphabetic small letters, a to h, along one 144 of the width-wise sides of the sheet 136, so as to indicate the corresponding length-wise lines 140. As shown in FIG. 3, the external surface of a first housing 114 of a sensor probe 112 is marked with two first indicias 146 (only one is shown; the other first indicia 146 is indicated on the opposite side wall of the first housing 114), and one second indicia 148, such that the foot of the second indicia 148 onto a straight line segment connecting between the two first indicias 146 coincides with an initial position of the sensor 32 to which the sensor 32 is moved when the present apparatus (or sensor probe 112) is initialized upon application of electric power thereto and turn-ON operation of a START switch (not shown of the apparatus.

A nurse or doctor places the elastic sheet 136 on the skin surface 23 of the patient, and finds by palpation or touch via the sheet 136 a suitable position directly above the radial artery 28 from which pressure pulse wave is to be detected. This position is identified by a pair of straight lines one of which is one of the width-wise lines A to N and the other of which is one of the length-wise lines a to h. Then, the sensor probe 112 is set on the sheet 136 on the skin surface 23 so that the two first indicias 146 are aligned with the specified one width-wise straight line (A to N) and such that the second indicia 148 is aligned with the specified one length-wise straight line (a to h). Thus, the positioning of the probe 112 on the wrist 10, specifically the positioning of the sensor 32 relative to the radial artery 28, is achieved in an easy and accurate manner.

While the present invention has been described in its preferred embodiments, the invention may otherwise be embodied.

For example, while in the embodiment of FIG. 1 the elastic sheet 36 has a surface area permitting the sensor probe 12 as a whole to contact the skin surface 23 via the sheet 36, it is required according to the principle of the present invention that the sheet 36 have a surface area permitting at least the sensor 32 to contact the skin surface 23 via the sheet 36. This arrangement also provides the advantages described previously with respect to the embodiment of FIG. 1, that is, reducing the pain or discomfort of the patient due to the pressed contact of the sensor 32 with the skin surface 23, preventing the sensor 32 from moving or slipping out of position on even a thin patient, and preventing a hairy skin from adversely influencing the pulse wave signal generated from the sensor 32.

In addition, although in the illustrated embodiments the elastic sheet 36, 136 is formed of silicone rubber, the elastic sheet may be formed of other rubbers such as natural rubber or urethane rubber, or a resin. It is possible that the elastic sheet be formed of a transparent material.

While in the illustrated embodiments the elastic sheet 36, 136 is simply placed on the skin surface 23 of the subject, it is possible to apply an adhesive to one of the opposite surfaces of the sheet 36, 136 which contacts the skin surface 23. Alternatively, in the case where the wrist 10 on which the sensor 32 is worn is fixed to a wrist bracing device, it is possible to secure the sheet 36, 136 to the wrist bracing device with the help of a band or the like. In these arrangements, too, the sheet 36, 136 is prevented against accidental movement or slipping out of place on the skin surface 23 of the subject.

In the embodiment of FIG. 1, the casing 24 supporting the sensor 32, or the sensor 32 itself, may be held in pressed contact with the skin surface 23 of the subject via the sheet 36 with the help of a wrist band. In these arrangements, too, the sheet 36 provides the various advantages proper to the present invention.

Although in the embodiment of FIG. 1 a plurality of pressure sensing elements are provided in the press surface 34 of the sensor 32, a pressure pulse wave sensor having a single pressure sensing element in a press surface thereof, may be employed to provide the same advantages as described previously.

It goes without saying that the present invention is applicable to the case where pressure pulse wave is detected by the sensor 32 from an arterial vessel different from the radial artery 28, such as a pedal dorsal artery.

It is to be understood that the present invention may be embodied with other changes, improvements and modifications that may occur to those skilled in the art without departing from the spirit and scope of the invention defined in the appended claims.

What is claimed is:

1. A pressure pulse wave transmitting sheet for being interposed between a skin surface of a living subject and a pressure pulse wave sensor set on the skin surface in pressed contact therewith, the sensor having a press surface in which an array of pressure sensing elements are provided and which is pressed against the skin surface so that a wall of an artery of the subject underlying the skin surface is partially flattened and that at least one of the pressure sensing elements detects a pressure pulse wave which is produced from the artery in synchronism with a heartbeat of the subject and is transmitted through the flattened wall of the artery and the skin surface, to the press surface of the sensor via the sheet, said pressure pulse wave transmitting sheet being formed of an elastic material having a hardness ranging from about 1 degree to about 15 degrees measured by a Japanese Industrial Standard (JIS) A-type spring-using hardness measuring device, said sheet having a plurality of first parallel straight lines which are provided on one of opposite surfaces of the sheet, and a plurality of second parallel straight lines each of which is provided on said one surface of the sheet so as to perpendicularly intersect said first straight lines, each of said first straight lines being indicated by a corresponding one of a first series of different indicias provided on said one surface of the sheet, each of said second straight lines being indicated by a corresponding one of a second series of different indicias provided on said one surface of the sheet.

2. The pressure pulse wave transmitting sheet as set forth in claim 1, wherein the sheet has a constant thickness of about 0.6 mm to about 3.0 mm.

3. The pressure pulse wave transmitting sheet as set forth in claim 2, wherein the sheet has a constant thickness of about 0.6 mm to about 1.0 mm.

4. The pressure pulse wave transmitting sheet as set forth in claim 1, wherein the sheet has a hardness of about 5 degrees to about 15 degrees measured by said JIS A-type spring-sing hardness measuring device.

5. The pressure pulse wave transmitting sheet as set forth in claim 1, wherein the sheet is formed of a rubber.

6. The pressure pulse wave transmitting sheet as set forth in claim 5, wherein said rubber is selected from the group consisting of silicone rubber, natural rubber, and urethane rubber.

7. The pressure pulse wave transmitting sheet as set forth in claim 1, wherein the sheet is formed of a resin.

8. The pressure pulse wave transmitting sheet as set forth in claim 1, wherein the sheet is formed of a transparent material.

9. The pressure pulse wave transmitting sheet as set forth in claim 1, wherein the sheet has a shape of a rectangle, and has said first series of different indicias provided along one side of one pair of opposite sides of said rectangle thereof, said pair of opposite sides being perpendicular to said first straight lines, and said second series of different indicias provided along one side of the other pair of opposite sides of said rectangle thereof, said other pair of opposite sides being perpendicular to said second straight lines.

10. An apparatus for detecting a pressure pulse wave of a living subject, comprising:
    a pressure pulse wave sensor adapted to be set on a skin surface of said subject in pressed contact therewith, said sensor having a press surface in which an array of pressure sensing elements are provided;
    a pressure pulse wave transmitting sheet adapted to be interposed between said skin surface of said subject and said press surface of said pressure pulse wave sensor, said sheet being formed of an elastic material having a hardness ranging from about 1 degree to about 15 degrees measured by a Japanese Industrial Standard (JIS) A-type spring-using hardness measuring device; and pressing means having an actuator for pressing said sensor against said skin surface so that a wall of an artery of said subject underlying said skin surface is partially flattened and that at least one of said pressure sensing elements detects a pressure pulse wave which is produced from said artery in synchronism with a heartbeat of said subject and is transmitted through the flattened wall of said artery and said skin surface, to said press surface of said sensor via said sheet.

11. The apparatus as set forth in claim 10, wherein said array of pressure sensing elements comprises at least one pressure sensing diode.

12. The apparatus as set forth in claim 10, wherein said actuator of said pressing means comprises:

a flexible diaphragm to which said sensor is secured; and means cooperating with said diaphragm for defining a pressure chamber filled with a fluid, said sensor being pressed against said skin surface via said sheet when fluid pressure in said pressure chamber is increased.

13. The apparatus as set forth in claim 10, wherein said pressing means comprises a band for pressing said sensor against said skin surface via said sheet.

14. The apparatus as set forth in claim 10, further comprising a housing supporting said sensor and said pressing means, said housing having an external surface on which at least two indicias are provided, one of opposite surfaces of said sheet having a surface area greater than said external surface of said housing, thereby allowing said housing to be entirely set on said one surface of the sheet, said sheet having a plurality of first parallel straight lines which are provided on said one surface of the sheet, and a plurality of second parallel straight lines each of which is provided on said one surface of the sheet so as to perpendicularly intersect said first straight lines, each of said first straight lines being indicated by a corresponding one of a first series of different indicias provided on said one surface of the sheet, each of said second straight lines being indicated by a corresponding one of a second series of different indicias provided on said one surface of the sheet, said housing being set on said skin surface via said sheet such that at least one of said at least two indicias on said external surface of said housing is aligned with a desired one of said first straight lines and another of said at least two indicias on said external surface of said housing is aligned with a desired one of said second straight lines.

15. The apparatus as set forth in claim 14, wherein said sheet has a a shape of a rectangle, and has said first series of different indicias provided along one side of one pair of opposite sides of said rectangle thereof, said one pair of sides being perpendicular to said first straight lines, and said second series of different indicias provided along one side of the other pair of opposite sides of said rectangle thereof, said other pair of sides being perpendicular to said second straight lines.

* * * * *